United States Patent [19]

Nagatsuka et al.

[11] Patent Number: 4,885,465

[45] Date of Patent: Dec. 5, 1989

[54] SPECTRUM DISPLAY DEVICE FOR X-RAY MICROANALYZER OR THE LIKE

[75] Inventors: Yoshitaka Nagatsuka; Masaki Saito; Yoshitaka Kawabe, all of Tokyo, Japan

[73] Assignee: JEOL, Ltd., Tokyo, Japan

[21] Appl. No.: 215,222

[22] Filed: Jul. 5, 1988

[30] Foreign Application Priority Data

Jul. 10, 1987 [JP] Japan .............................. 62-172358

[51] Int. Cl.⁴ .......................................... G01N 23/04
[52] U.S. Cl. ................................... 250/310; 250/306; 250/397; 378/45; 378/88; 340/720
[58] Field of Search ............... 250/307, 310, 306, 397; 340/720, 721, 722; 378/45, 49, 82–85, 88

[56] References Cited

U.S. PATENT DOCUMENTS

| | | | |
|---|---|---|---|
| 3,150,261 | 9/1964 | Furbee et al. | 378/46 |
| 3,914,605 | 10/1975 | Hara | 250/276 |
| 4,037,101 | 7/1977 | Okumura et al. | 250/307 |
| 4,253,154 | 2/1981 | Russ et al. | 364/527 |
| 4,438,332 | 3/1984 | Lichtenegger | 250/310 |
| 4,586,036 | 4/1986 | Thomason et al. | 340/720 |
| 4,697,080 | 9/1987 | King | 250/307 |

Primary Examiner—Carolyn E. Fields
Assistant Examiner—John A. Miller
Attorney, Agent, or Firm—Webb, Burden, Ziesenheim & Webb

[57] ABSTRACT

A display for an x-ray microanalyzer including a wavelength-dispersive x-ray spectrometer and an energy-dispersive x-ray spectrometer for producing two kinds of spectra from the same region on a specimen. A circuit enables markers to be superimposed on the spectra to indicates some wavelengths and energies of the characteristic x-ray emanating from a chemical element selected by the operator. The markers faciliatate precisely confirming the existence of the element in the region, based on the two kinds of spectra.

3 Claims, 2 Drawing Sheets

SPECTRUM DISPLAY DEVICE FOR X-RAY MICROANALYZER OR THE LIKE

BACKGROUND OF THE INVENTION

The present invention relates to an electron probe microanalyzer (or x-ray microanalyzer) or the like which equips with a wavelength-dispersive x-ray spectrometer and an energy dispersive x-ray spectrometer and, more particularly, to a spectrum display device which is for use with such an electron probe microanalyzer and on which two kinds of x-ray spectra are displayed according to the detected signals coming from the two x-ray spectrometers.

An electron probe microanalyzer or the like incorporates both a wavelength-dispersive x-ray spectrometer as disclosed in U.S. Pat. No. 3,914,605 and an energy-dispersive x-ray spectrometer as disclosed in U.S. Pat. Nos. 4,253,154 and 4,697,080. A specimen placed in the microanalyzer is irradiated with an electron probe. Then, characteristic x-rays emanating from the specimen are detected, and an x-ray spectrum is displayed according to the result of the detection. Thus, the elements included in the specimen are identified.

These two kinds of x-ray spectrometers for detecting characteristic x-rays emitted from a specimen have different features. In particular, the wavelength-dispersive x-ray spectrometer exhibits high resolution in terms of wavelengths, but it cannot easily remove higher-order x-rays it entails. On the other hand, the spectrum from the energy-dispersive x-ray spectrometer has no higher-order x-rays, but it shows poor energy resolution. Especially, it cannot easily detect quite light elements, for example, in the range from Be (beryllium) to F (fluorine).

Accordingly, it is the common practice that x-ray spectra obtained by the two kinds of spectrometers are separately displayed on a display device to identify elements. When a wavelength spectrum derived by the wavelength-dispersive spectrometer is displayed, the operator might misidentify the included elements because of higher-order x-rays. Meanwhile, when an energy spectrum obtained by the energy-dispersive spectrometer is displayed, peaks tend to overlap due to poor energy resolution. As a result, the operator might overlook some elements included.

SUMMARY OF THE INVENTION

It is a main object of the present invention to provide a spectrum display device which is for use with an x-ray microanalyzer or the like and on which two kinds of x-ray spectra obtained from a wavelength-dispersive x-ray spectrometer and an energy-dispersive x-ray spectrometer are displayed simultaneously, whereby making qualitative analyses with improved accuracy.

It is another object of the invention to provide a spectrum display device which is for use with an x-ray microanalyzer or the like and on which two kinds of x-ray spectra obtained from a wavelength-dispersive x-ray spectrometer and an energy-dispersive x-ray spectrometer are simultaneously displayed together with markers that permit one to easily know the relation between the two kinds of spectra.

These objects are achieved by a spectrum display device for use with an electron probe microanalyzer or the like which irradiates the surface of a specimen with an electron beam and comprises a wavelength-dispersive x-ray spectrometer and an energy-dispersive spectrometer. The display device comprises a viewing surface upon which spectra obtained from the same region on the specimen by the two kinds of spectrometers are simultaneously displayed. Circuitry superimposes markers on the spectra presently displayed. The markers indicate the energies and wavelengths of some lines, such as the K, L, and M lines, of the characteristic x-rays emanating from the specimen. Controls are provided for moving the positions of the markers in an interrelated manner such that some of the markers indicate the energies of the lines, while the other indicate the wavelengths of the lines.

Other objects and features of the invention will appear in the course of the description thereof which follows.

DESCRIPTION OF THE PREFERRED EMBODIMENT

Figure 1:
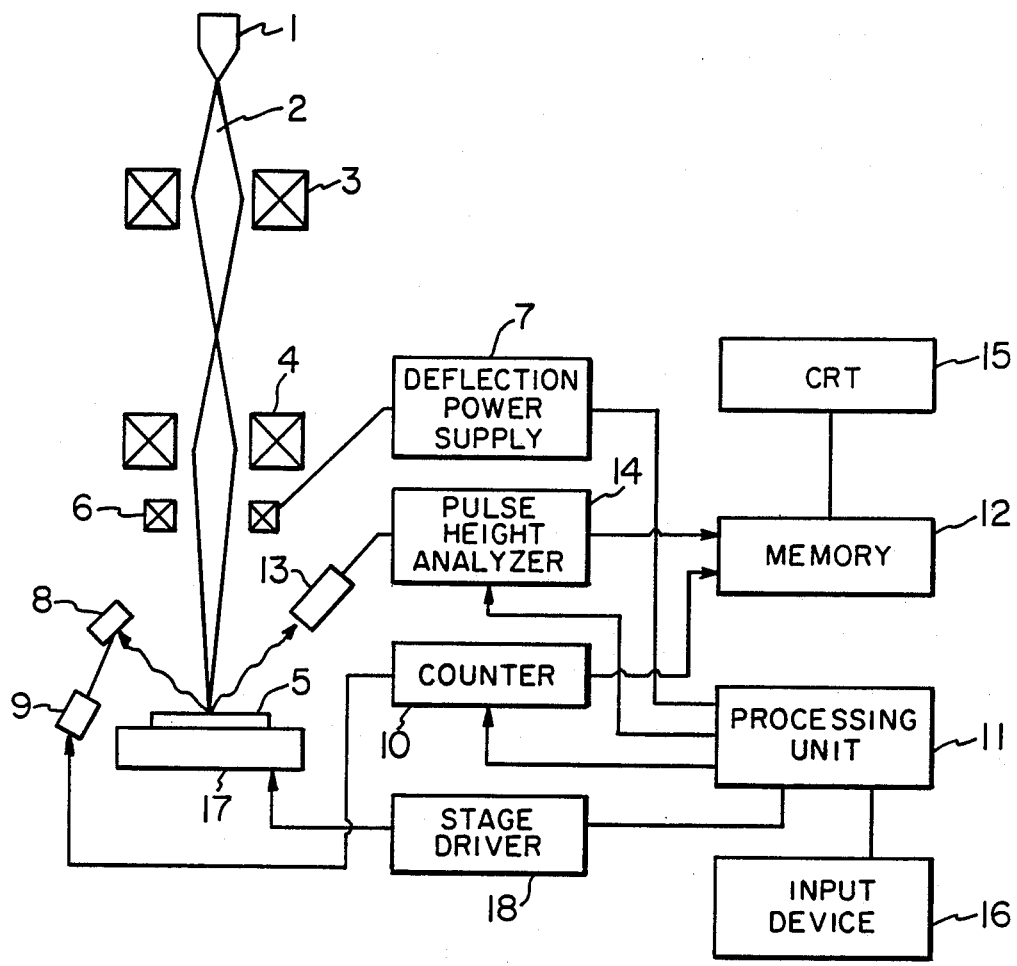
FIG. 1 is a schematic block diagram of an x-ray microanalyzer equipped with a spectrum display device according to the invention.

Referring to FIG. 1, an x-ray microanalyzer according to the invention is schematically shown. This microanalyzer includes an electron gun 1 that produces an electron beam 2. This beam 2 is focused sharply by a condenser lens 3 and a final stage condenser lens 4 and directed onto a specimen 5. An electron beam-scanning coil 6 that is supplied with deflecting current from a deflecting power supply 7 which permits the operator to arbitrarily select the irradiated position on the specimen 5 or causes the beam 2 to make a two-dimensional scan of the specimen. A spectral crystal (or analyzing crystal) 8 diffracts only certain wavelengths of x-rays emanating from the specimen 5 to an x-ray detector 9. In the present example, a plurality of such spectral crystals are mounted, and only one selected crystal is employed at a time. The output pulses from the detector 9 are amplified by an amplifier (not shown) and fed to a counter 10, which counts its input pulses for a time set by a control signal from a processing unit 11. The total count obtained by the counter 10 is stored in a memory 12 as a wavelength spectrum derived by the wavelength-dispersive spectrometer (WDS).

X-rays produced from the specimen 5 are also detected by a semiconductor detector 13 forming an energy-dispersive spectrometer (EDS). The detector 13 produces voltage pulses having amplitudes corresponding to the energies of the incident x-rays. The voltage pulses from the detector 13 are furnished to a multichannel pulse-height analyzer 14 via an amplifier (not shown). The analyzer 14 sorts the output pulses from the detector 13 into selected range of amplitude and counts the numbers of the pulses falling into their respective ranges. These numbers representing an energy spectrum are placed in storage locations within the memory 12 assigned to the ranges, under the control of the processing unit 11. X-ray spectra are displayed on a cathode-ray tube 15. An input device 16 such as a keyboard is connected with the processing unit 11. The specimen 5 is placed on a specimen stage 17 which can be driven by a stage-driving circuit 18 in accordance with a control signal from the processing unit 11.

In the instrument constructed in this way, x-rays detected by the two kinds of spectrometers (WDS and EDS) are displayed on the same screen of the CRT 15 in the form of x-ray spectra. Then, the operator can identify the elements contained in the specimen. This procedure is next described in greater detail.

The specimen 5 produces x-rays in response to the irradiation of the electron beam 2. The x-rays are detected by the two kinds of spectrometers. In the wavelength-dispersive spectrometer, the spectral (or analyzing) wavelength is swept from the shortest wavelength to the longest wavelength or vice versa to obtain an x-ray spectrum. In the energy-dispersive spectrometer, the x-rays originating from the specimen 5 are detected by the semiconductor detector 13, which then converts the energies of the incident x-ray photons into corresponding voltage pulses. Subsequently, the multiohannel pulse-height analyzer 14 gives rise to an energy spectrum according to the voltage pulses.

Figure 2:
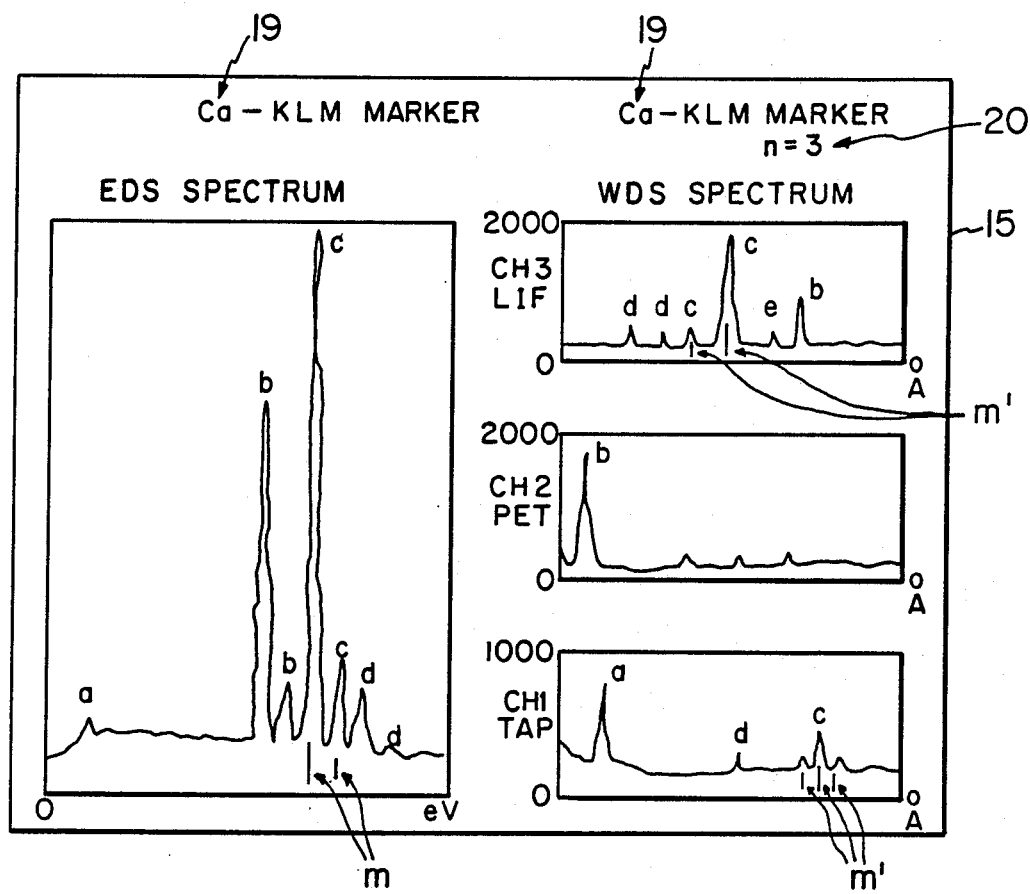
FIG. 2 shows the face of the display device shown in FIG. 1.

Referring next to FIG. 2, the novel instrument is characterized in that wavelength spectra and an energy spectrum are displayed simultaneously on the CRT 15 together with markers. In the wavelength and energy spectra, the x-ray intensity is plotted with regard to wavelength and energy, respectively. The markers superimposed on the energy spectrum indicate certain energies, while the markers displayed on the wavelength spectrum indicate given wavelengths. Those markers which indicate the characteristic x-rays emanating from the same element are moved in an interrelated manner.

Referring also to FIG. 1, when some display conditions are entered from the input device 16, the processing unit 1; reads corresponding energy spectrum and wavelength spectra from the memory 12 and presents these spectra on the CRT 15 simultaneously. More specifically, the energy spectrum obtained by the energy-dispersive spectrometer (EDS) is shown on the left half of the screen of the CRT 15 (FIG. 2). The wavelength spectra obtained by using the wavelength-dispersive spectometer (WDS) are displayed on the right half of the screen.

In this specific example, one energy spectrum and three wavelength spectra are displayed on the CRT 15. After collecting data from the wavelength-dispersive spectrometers, it is not always necessary to display all the wavelength spectra. Only the desired one or more of the spectra need be displayed, and the details of the spectrum can be observed. Also, the vertical and horizontal axes of each spectrum can be enlarged or reduced. Similarly, the vertical and horizontal axes of each energy spectrum can be either enlarged or reduced. If some chemical elements, such as elements a-e, are identified using a wavelength spectra obtained by WDS, then the name of the identified elements are displayed at the positions of their respective wavelengths on the wavelength spectrum on the CRT 15. If some elements, such as elements a-d, are identified using an energy spectrum obtained by EDS, then the names of the identified elements are displayed at the positions of their respective energies.

It is now assumed that the name or atomic number of an elements, such as Ca, is entered from the input device 16, KLM markers m are displayed on the energy spectrum at the positions of the energies of the K, L, and M lines of the characteristic x-rays emanating from the element Ca. In response to this, KLM markers m, are displayed on the wavelength spectrum at the positions of the first to n-th order lines of the characteristic x-ray emanating from the element Ca. The reverse procedure is also possible. That is, either the name or the atomic number of an element, such as Ca, is entered from the input device 16. Then KLM markers m, are displayed on the wavelength spectrum at the positions of the wavelengths of the first to n-th order lines of the characteristic x-rays emanating from the element Ca. In response to this, KLM markers m are displayed on the energy spectrum at the positions of the energies of the K, L, and M lines of the characteristic x-rays emanating from Ca. When the element Ca is designated, the symbol of the element is displayed on the screen of the CRT 15 as indicated by numeral 19. Further, the 3rd order designated from the input device 16 is displayed on the screen in the form of "n=3" as indicated by numeral 20.

A wavelength spectra and energy spectrum are displayed on the CRT 15 at the same time, and elements are identified on the principles described below.

(1) If the existence of any element can be inferred from both wavelength and energy spectra displayed, then it is determined that the element exists in the specimen.

(2) If the existence of any element is provisionally inferred from an energy spectrum but a wavelength spectrum does not suggest its pesence, then the KLM markers for the other elements already identified using energy and/or wavelength spectra are displayed. If these markers are close to the position of peaks on the energy spectrum, then the provisional inference from the energy spectrum is negated, i.e., the elements is judged to be absent.

(3) Conversely, if the existence of element is provisionally inferred from a wavelength spectrum but an energy spectrum does not support it, then the KLM markers for higher-order lines of the characteristic x-rays arising from other identified elements are displayed on the wavelength spectrum. If the markers are placed closed to positions of the peaks on the wavelength spectrum, then the provisionally inferred element is judged to be absent.

(4) If those peaks of a wavelength spectrum which are positioned at locations where quite light elements, such as carbon and boron, should appear coincide with none of the higher-order lines of the characteristic x-rays of any other identified element, they are judged to be the peaks of the quite light elements incapable of being detected with the energy-dispersive spectrometers.

When plural spectra as mentioned above are displayed and compared for examination, if it is necessary to scrutinize very small portions of the spectra, then the vertical or horizontal axis of each spectrum may be extended.

In the present example, it is not always required that the wavelength spectrum obtained by the wavelength-dispersive spectrometer be plotted with regard to wavelength. For example, the spectrum may also be plotted against the position of the spectrometer corresponding to wavelength or against the value converted from energy. Also in the latter cases, the elements included in the specimen can be identified accurately.

Also in the present example, one energy spectrum and three wavelength spectra are displayed to identify the elements contained in the specimen. Of course, the numbers of the two kinds of spectra are not limited to these values.

Further in the present example, the energy spectrum obtained by the energy-dispersive spectrometer is displayed on the left half of the screen of the CRT 15 and, at the same time, the wavelength spectra derived the wavelength-dispersive spectrometer is displayed on the right half. The present invention is not restricted to this method of display. For instance, the energy spectrum may be displayed on the upper half of the screen, while the wavelength spectra may be displayed on the lower half. In this case, the energy axis of the energy spectrum may be aligned to the wavelength axis of the energy spectrum to facilitate comparing the two kinds of spectra.

In addition, in the present example, the KLM markers consist of solid lines. Alternatively, the K, L, and M markers are made up of a solid line, a broken line, a dot-and-dash line, respectively. Furthermore, the markers may be displayed in different colors.

As described in detail thus far, in accordance with the invention, two kinds of x-ray spectra respectively obtained by a wavelength-dispersive spectrometer and an energy-dispersive spectrometer are displayed on the same viewing screen. Markers indicating energies and wavelengths are superimposed on the spectra. The positions of two kinds of markers are varied in an interrelated manner so as to indicate energy and wavelength. This allows the elements contained in the specimen to be identified accurately and analyzed quantitatively.

Having thus described our invention with the detail and particularity required by the Patent Laws, what is desired and claimed protected by Letters Patent is set forth in the following claims.

What is claimed is:

1. A apectrum display device for use with an electron beam device which irradiates the surface of a specimen with an electron beam to produce x-rays from the specimen and includes a wavelength-dispersive x-ray spectrometer, and an energy-dispersive x-ray spectrometer, said display device comprising:
    a display means having a viewing screen on which spectra obtained from the same region on the specimen by the two x-ray spectrometers are simultaneourly displayed;
    an input device for permitting one to designate a desired chemical element; and
    said spectrum display device including means which superimposes markers on the spectra displayed on the display means, the markers indicating the energies and wavelength of characteristic x-rays emanating from the element designated by the designation means.

2. The spectrum display device of claim 1, wherein the markers are displayed in different colors or patterns according to the kinds of spectral lines, of the characteristic x-ray which are indicated by the markers.

3. A spectrum display device for use with an electron beam device which irradiates the surface of a specimen with an electron beam to produce x-rays from the specimen and includes a wavelength-dispersive x-ray spectrometer, and an energy-dispersive x-ray spectrometer, said display device comprising:
    a display means having a viewing screen on which spectra obtained from the same region on the specimen by the two x-ray spectrometers are displayed;
    an input device for permitting one to designate a desired chemical element;
    said spectrum display device including a means for displaying the name of the designated element on the display means; and
    a means which superimposes markers on the spectra displayed on the display means, the markers indicating the energies and wavelength of the characteristic x-rays emanating from the element designated by the designating means.

* * * * *

UNITED STATES PATENT AND TRADEMARK OFFICE
CERTIFICATE OF CORRECTION

PATENT NO. : 4,885,465
DATED : December 5, 1989
INVENTOR(S) : Yoshitaka Nagatsuka, Masaki Saito and Kazuyasu Kawabe It is certified that error appears in the above-identified patent and that said Letters Patent is hereby corrected as shown below:

On the title page:

Under Inventors "Yoshitaka Kawabe" should read --Kazuyasu Kawabe--.

Column 3 Line 67 "m," should read --m'--.

Claim 1 Line 35 Column 5 "apectrum" should read --spectrum--.

Claim 1 Lines 13-14 Column 6 "designation" should read --designating--.

Signed and Sealed this

Ninth Day of October, 1990

*Attest:*

HARRY F. MANBECK, JR.

*Attesting Officer*      *Commissioner of Patents and Trademarks*